(12) United States Patent
Eklund et al.

(10) Patent No.: US 8,962,862 B2
(45) Date of Patent: Feb. 24, 2015

(54) PROCESSES FOR PREPARING 4-SUBSTITUTED IMIDAZOLES

(75) Inventors: Lars Eklund, Karlskoga (SE); Lars Hansson, Karlskoga (SE); Tommy Lundholm, Karlskoga (SE); Pär Holmberg, Karlskoga (SE); Margus Eek, Tallinn (EE)

(73) Assignee: Cambrex Karlskoga AB, Karlskoga (SE)

( * ) Notice: Subject to any disclaimer, the term of this patent is extended or adjusted under 35 U.S.C. 154(b) by 0 days.

(21) Appl. No.: 14/234,263

(22) PCT Filed: Jul. 20, 2012

(86) PCT No.: PCT/GB2012/051746
§ 371 (c)(1),
(2), (4) Date: Mar. 12, 2014

(87) PCT Pub. No.: WO2013/014428
PCT Pub. Date: Jan. 31, 2013

(65) Prior Publication Data
US 2014/0187789 A1    Jul. 3, 2014

Related U.S. Application Data

(60) Provisional application No. 61/510,538, filed on Jul. 22, 2011.

(51) Int. Cl.
| | | |
|---|---|---|
| C07D 233/58 | (2006.01) | |
| C07F 5/04 | (2006.01) | |
| C07C 47/228 | (2006.01) | |
| C07F 5/02 | (2006.01) | |
| C07C 45/63 | (2006.01) | |
| C07C 47/24 | (2006.01) | |
| C07C 47/11 | (2006.01) | |

(52) U.S. Cl.
CPC .............. *C07D 233/58* (2013.01); *C07F 5/025* (2013.01); *C07C 45/63* (2013.01); *C07C 47/24* (2013.01); *C07C 47/11* (2013.01)
USPC .......................... 548/346.1; 549/213; 568/425

(58) Field of Classification Search
None
See application file for complete search history.

(56) References Cited

FOREIGN PATENT DOCUMENTS

| CN | 101921234 A | 12/2010 |
|---|---|---|
| EP | 1918282 A1 | 5/2008 |
| GB | 2101114 A | 1/1983 |
| WO | 2009053709 A1 | 4/2009 |
| WO | 2011070069 A1 | 6/2011 |

OTHER PUBLICATIONS

Yan, et al., Chem. Comm., 46:3170 (2010).*
Guobing Yan et al, "Nano Fe2O3 catalyzed direct borylation of arenes", Chemical Communications, vol. 46, Mar. 10, 2010, pp. 3170-3172, XP002685973, Entry 5 in table 2; p. 3171.
International Search Report and Written Opinion mailed Nov. 13, 2012 (PCT/GB2012/051746); ISA/EP.

* cited by examiner

*Primary Examiner* — Michael Barker
(74) *Attorney, Agent, or Firm* — Banner & Witcoff, Ltd.

(57) ABSTRACT

There is provided a novel process for the preparation of a compound of formula (I), (Formula (I)). There is also provided novel processes to intermediates of the compound of formula (I), as well as novel intermediates themselves.

(I)

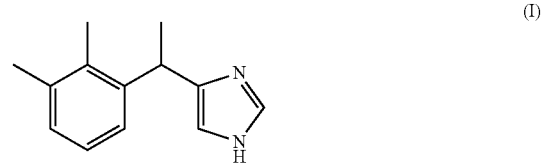

15 Claims, No Drawings

PROCESSES FOR PREPARING 4-SUBSTITUTED IMIDAZOLES

The present invention relates to a new process. In particular, it relates to a new process in the preparation of known compounds that have a 4-substituted imidazole core, for instance medetomidine and variants thereof that may have been employed as the active ingredient in antifouling products such as Selectope™. The invention also relates to the production of new compound intermediates.

The majority of previously known routes to medetomidine are based on syntheses starting from compounds in which the imidazole ring is already formed. For instance, international patent application WO 2009/053709, European patent application EP 1 918 282, UK patent application GB 2 101 114 and Chinese patent application 101921234 all disclose examples of such syntheses. International patent application WO 2011/070069 discloses a process for the preparation of medetomidine, in which one of the starting materials is 2,3-dimethylbenzoic acid. The process sequence contains numerous synthetic steps (about seven), one of which involves an imidazole ring-forming reaction step. The imidazole ring-forming reaction has a specific diamine precursor, and the resulting product contains an imidazole ring substituted with a benzyl group (which needs to be removed) and which is a to a carbonyl group (which has to be modified to an alkene and then reduced).

The present invention circumvents the potentially disadvantageous use of imidazole derivatives as starting materials.

There are also several other disadvantages with previous syntheses of medetomidine (and the like). Previously disclosed processes may be disadvantageous from an economic or environmental point of view. They may also be disadvantageous from the point of view of efficiency and scalability. All these factors are crucial for processes that need to be conducted on an industrial scale.

In summary, there are only a limited number of processes known for the preparation of certain 4-substituted imidazole deriviates (e.g. medetomidine). There is therefore a need for alternative and/or improved processes.

The listing or discussion of an apparently prior-published document in this specification should not necessarily be taken as an acknowledgement that the document is part of the state of the art or common general knowledge.

In a first aspect of the invention, there is now provided a process for the preparation of a compound of formula I,

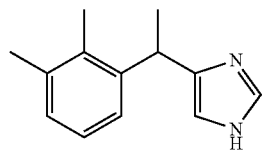

I which process comprises reaction of a compound of formula II,

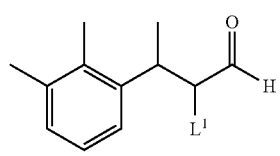

II wherein:
$L^1$ represents a suitable leaving group, such as a suitable halo group (e.g. bromo), a sulfonate group (e.g. —OS(O)$_2$C$_{1-12}$ alkyl or —OS(O)$_2$aryl/heteroaryl, such as —OS(O)$_2$CF$_3$, —OS(O)$_2$CH$_3$ or —OS(O)$_2$PhMe), an oxy-acyl group (e.g. —O—C(O)—C$_{1-12}$ alkyl, such as acetoxy) or the like, in the presence of:

(a) a source of formamidine, such as formamidine (or a salt or derivative thereof, such as formamidine acetate, formamidine hydrohalide and/or formamidinesulfinic acid) or a mixture of an ammonium salt (e.g. an ammonium halide, such as ammonium chloride) and formic acid; or (b) formamide, which process is hereinafter referred to as "the process of the invention".

The process of the invention may be performed employing salts, solvates or protected derivatives (of compounds of formula II), thereby producing compounds that may or may not be produced in the form of a (e.g. corresponding) salt or solvate, or a protected derivative thereof (of compounds of formula I).

The protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

Similarly, the compounds employed in or produced by the processes described herein (i.e. those involving the process of the invention) may also contain one or more asymmetric carbon atoms and may therefore exist as enantiomers or diastereoisomers, and may exhibit optical activity. The process of the invention thus encompasses the use or production of such compounds in any of their optical or diastereoisomeric forms, or in mixtures of any such forms.

Further, the compounds employed in or produced by the processes described herein (e.g. compounds of formula IIA as hereinbefore defined) may contain double bonds and may thus exist as E (entgegen) and Z (zusammen) geometric isomers about each individual double bond. All such isomers and mixtures thereof are included within the scope of the invention.

Unless otherwise specified, alkyl and alkoxy (i.e. —O-alkyl) groups as defined herein may be straight-chain or, when there is a sufficient number (i.e. a minimum of three) of carbon atoms be branched-chain, and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated. Additionally, alkyl groups may be referred to as optionally substituted (although they are preferably unsubstituted), for instance with one or more substituents selected from halo (e.g. fluoro), —CN and $C_{1-6}$ alkoxy, in which the alkyl moiety of the alkoxy group is optionally substituted by one or more fluoro atoms. In particular, alkyl groups may be optionally substituted with one or more fluoro atoms (or unsubstituted).

Unless otherwise specified, alkylene groups as defined herein may be straight-chain or, when there is a sufficient number (i.e. a minimum of two) of carbon atoms, be branched. In particular, alkylene may refer to straight-chain alkylene groups. Additionally, alkylene groups may be referred to as optionally substituted (although they are preferably unsubstituted), for instance with one or more substituents selected from halo (e.g. fluoro), —CN and $C_{1-6}$ alkoxy, in which the alkyl moiety of the alkoxy group is optionally substituted by one or more fluoro atoms. In particular, alkylene groups may be optionally substituted with one or more fluoro atoms (or unsubstituted).

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, and the like. For the avoidance of doubt, the point of attachment of substituents on aryl groups may be via any carbon atom of the ring system. The term "heteroaryl", when used herein, includes 5- to 14-membered heteroaryl groups containing one or more heteroatoms selected from oxygen, nitrogen and/or sulfur. Such heteroaryl group may comprise one, two or three rings, of which at least one is aromatic. Substituents on heteroaryl groups may, where appropriate, be located on any atom in the ring system including a heteroatom. The point of attachment of heteroaryl groups may be via any atom in the ring system including (where appropriate) a heteroatom. Additionally, such aryl/heteroaryl groups are also optionally substituted (although they are preferably unsubstituted), for instance with one or more substituents selected from halo, —CN, $C_{1-6}$ alkyl and $C_{1-6}$ alkoxy (in which the alkyl moiety of the alkyl/alkoxy group is optionally substituted by one or more fluoro atoms).

The term "halo", when used herein, includes fluoro, chloro, bromo and iodo.

As used herein, the term "heterocycloalkyl" refers to cyclic alkyl groups containing at least one heteroatom (in particular, at least one atom selected from O, S and N). In particular, such groups may be monocyclic. Such heterocycloalkyl groups as referred to herein may be referred to as optionally substituted (although they are preferably unsubstituted), for instance with one or more substituents selected from halo, —CN, $C_{1-6}$ alkyl and $C_{1-6}$ alkoxy (in which the alkyl moiety of the alkyl/alkoxy group is optionally substituted by one or more fluoro atoms). In particular, heterocycloalkyl groups as referred to herein are optionally substituted with one or more fluoro atoms (or unsubstituted).

The process of the invention is preferably performed in the presence of a source of formamidine (e.g. formamidine, or an appropriate salt or derivative thereof). Most preferably, it is performed in the presence of formamidine acetate, although other derivatives are also possible, for instance other salts such as formamidine hydrohalide (e.g. HCl), formamidine-sulfinic acid and/or other salts or derivatives that may be commercially available). Formamidine and, in particular, formamidine acetate may have the advantage that the process of the invention is improved, e.g. in terms of yield and purity.

Thus, in a particular embodiment that may be mentioned, the process is performed in the presence of formamidine acetate.

In a particular embodiment that may be mentioned, $L^1$ represents a suitable halo group (in particular, bromo).

Preferably, at least one equivalent of the reagent that promotes the imidazole ring-forming reaction (e.g. formamidine acetate) is employed compared to the compound of formula II (as otherwise, the reaction may not proceed to completion, thus compromising yield), such as from about 1.1 to about 2.5 equivalents, for instance about 1.5 equivalents or about 2 equivalents. The preferred number of equivalents maximises the efficiency and potential yield of the product to be formed.

The process of the invention may be performed in the presence of a suitable solvent, such as a polar organic solvent, for instance an alcoholic solvent. The most preferred solvents are ethanol and IPA (e.g. ethanol). The quantity of solvent, relative to the compound of formula II should be sufficient for the reaction to proceed efficiently. For instance, at least a 1:1 ratio of compound of formula II:alcoholic solvent (by weight) is employed, preferably a ratio of at least 1:2, such as at least 1:3. Although the ratio may be 1:10, it is preferred than the ratio is from 1:4 to 1:6 (e.g. between 1:4 and 1:6, such as about 1:5). More particularly, the ratio may be from 1:6 to 1:7 (e.g. between 1:6 and 1:7, such as about 1:7). Higher quantities of solvent have the disadvantage that the reaction rate may decrease due to the higher dilution and additionally may have environment/economical disadvantages.

In a particular embodiment that may be mentioned, the suitable solvent may be selected from ethanol, iso-propyl alcohol (IPA), or a mixture of ethanol or iso-propyl alcohol and water (such as an approximately equal mixture).

In a more particular embodiment, the suitable solvent is iso-propyl alcohol (IPA). In particular, a ratio of 1:7 of compound of formula II:IPA (by weight) may be employed.

Additionally, the process of the invention may be performed in the presence of a non-aqueous ionising solvent (in addition to the solvent that may already be present (e.g. the alcoholic solvent)). In this respect, the preferred additional solvent is liquid or aqueous ammonia (for instance, 25% aqueous ammonia may be employed). Compared to the compound of formula II, at least 1 molar equivalent of the non-ionising agent is employed (e.g. at least 5 molar equivalents, such as from 5 to 20 molar equivalents (e.g. between 5 and 20 molar equivalents), preferably about 10 molar equivalents). In terms of relative weights, compared to the primary solvent employed (e.g. the alcoholic solvent such as IPA), assuming the additional solvent is 25% aqueous ammonia, the ratio of primary solvent to additional solvent is from 1:2 to 10:1 (e.g. between 1:2 and 10:1), preferably from 1:1 to 5:1 (e.g. between 1:1 and 5:1, such as about 1.5:1 or 2:1).

In a particular embodiment that may be mentioned, the non-aqueous ionising solvent is liquid ammonia. In a more particular embodiment of the invention that may be mentioned, compared to the compound of formula II, from 5 to 20 molar equivalents of liquid ammonia are used (particularly from about 6 to about 16, such as from about 8 to about 15 (e.g. about 9 (such as about 8.9), about 12 or 13 (such as about 12.5) or about 14 (such as about 14.4) molar equivalents of liquid ammonia compared to the compound of formula II).

In a particular embodiment that may be mentioned, the primary solvent is IPA and the non-aqueous ionising solvent is liquid ammonia (i.e. the solvent used in the reaction is a mixture of IPA and liquid ammonia). For example, the reaction may be performed in solvent at least 90% (e.g. at least 95%, such as at least 99%) of which consists of a mixture of IPA and liquid ammonia.

More particularly, in terms of relative weights, the ratio of IPA to liquid ammonia is from 6:1 to 12:1, such as from about 8:1 to about 11:1 (e.g. about 11:1 or about 86:10). For example, the reaction may be performed in solvent mixture which is from 6 to 12% by weight of liquid ammonia in IPA (e.g. about 8.3% by weight or, particularly, about 10.4% by weight of liquid ammonia in IPA).

The process of the invention is preferably performed at elevated temperature, e.g. at above room temperature (e.g. at above 50° C., such as above 80° C., for instance at about 120°

C., depending on the boiling point of the solvent system that is employed) for a period of time (e.g. about 2 hours) although the temperature and reaction time may be varied in order to maximise reaction efficiency and yield. For example, where the solvent is a mixture of liquid ammonia and IPA (e.g. 10.4% by weight of liquid ammonia in IPA), the reaction may be performed at a temperature of from about 70 to about 90° C. (such as from about 75 to about 85° C., e.g. from about 77 to about 83° C.). In a particular embodiment that may be mentioned, the process of the invention may comprise the step of adding the compound of formula II to a preheated mixture comprising:

(a) some or all of the required solvent(s) (e.g. the mixture of IPA and liquid ammonia; for example, a mixture comprising at least 50% of the total solvent(s) used in the reaction); and
(b) the source of formamidine, such as formamidine (or a salt or derivative thereof, such as formamidine acetate, formamidine hydrohalide and/or formamidinesulfinic acid) or a mixture of an ammonium salt (e.g. an ammonium halide, such as ammonium chloride) and formic acid.

As used herein, the term "preheated" will be understood as referring to a mixture that, at the point of addition of the compound of formula II, is at elevated temperature, for example at above room temperature (e.g. at above 50° C., such as above 70° C. (e.g. from about 70 to about 120° C.), depending on the boiling point of the solvent system that is employed and the particular pressure that the reaction is performed at). For example, where the solvent is a mixture of liquid ammonia and IPA (e.g. 10.4% by weight of liquid ammonia in IPA), the preheated mixture may be at a temperature of from about 70 to about 90° C. (such as from about 75 to about 85° C., e.g. from about 77 to about 83° C.).

The process of the invention may be performed in a sealed container and, optionally, at elevated pressure (i.e. at greater than atmospheric pressure). As used herein, the term "sealed container" may refer to any means for containing the reaction (e.g. a reaction vessel) that prevents release of the contents thereof (e.g. the reaction components). Particular reaction vessels that may be mentioned include a sealed glass vial and a sealed steel container, such as a PTFE-lined bomb (i.e. a sealed metal container lined with polytetrafluoroethylene (PTFE)). In particular, the process may be performed in a sealed container and at elevated temperature and/or elevated pressure (e.g. wherein the container is sealed and then the contents heated to elevated temperature, thus resulting in the reaction being performed at elevated pressure).

After the process of the invention, the compound of formula I (or salt, solvate or other derivative thereof) may be isolated. For instance the solvent system (e.g. ammonia and IPA) may be removed (e.g. preferably at normal atmospheric pressure, for instance by boiling the solvent; although the solvent system may also be removed under reduced pressure, e.g. by distillation at reduced pressure) to leave a residue. The residue may be taken up in a mixture of water and organic solvent, or, in another embodiment, the residue may be added to water (in the latter embodiment, the crude product can simply be separated from the water layer, circumventing the need to employ organic solvent in that step).

When the residue is taken up in a mixture of water and organic solvent, then the organic solvent may be any non water-soluble organic solvent that dissolves the product (e.g. a polar organic solvent such as ethyl acetate, or a non-polar organic solvent such as an aromatic solvent, e.g. toluene). In this case, the pH of the mixture (the residue, water and organic solvent) may be adjusted to 9-10 (by employing e.g. a carbonate base, hydroxide base, alkoxide base or the like, e.g. sodium carbonate or sodium hydroxide) and the phases separated. The organic phase may then be washed with dilute hydrochloride acid so that the product is substantially in the aqueous phase. After the organic phase is separated, the pH of the aqueous phase (containing the product) may then be adjusted to pH 9-10 (by employing e.g. a carbonate base, hydroxide base, alkoxide base or the like, e.g. sodium carbonate or sodium hydroxide) and the product extracted again with organic solvent (e.g. a polar organic solvent, such as ethyl acetate, or a non-polar organic solvent such as an aromatic solvent, e.g. toluene). The water phase is separated and the organic phase concentrated to leave a residue containing the desired product.

The product of formula I may be isolated after the process of the invention as the free base. For example, the free base may be isolated as a solid (e.g. a crystalline solid), which may obtained via crystallisation from a suitable solvent (such as the organic solvent used in the extraction of the product).

Alternatively, the desired product of the compound of formula I may be isolated from the residue from the work up as a corresponding salt (e.g. the corresponding acid salt, such as a hydrogen halide, e.g. HCl), for instance by precipitation. Advantageously, the salt (e.g. HCl salt) of the compound of formula I may be solid (or even crystalline) and may therefore be easily isolated, for instance the residue may be taken up in an organic solvent (e.g. a polar aprotic organic solvent, such as acetone) and the precipitation of e.g. the hydrogen halide salt may be promoted by the addition of the hydrogen halide (e.g. hydrochloric acid, which may be concentrated, e.g. 37% HCl, or, gaseous HCl may be employed) to a lower pH (e.g. down to about pH 6). The product may be filtered and washed with more solvent (e.g. acetone). If desired, further product or a second crop of product (e.g. the HCl salt of the compound of formula I) may be isolated by the distillation of the solvent from the mother liquor followed by the addition of water free acetone. However, when gaseous HCl is employed in the hydrogen halide salt forming step, the isolation of a second crop of product (e.g. the HCl salt thereof) need not be performed.

If the product of formula I is isolated as the salt, the salt may then be converted to the free base by neutralising the salt. Reaction conditions that may be employed may be described in the examples (e.g. first the salt is dissolved in water and then treated with charcoal), for instance, the neutralisation may be performed by the addition of base (e.g. a hydroxide such as sodium hydroxide), e.g. at elevated temperature (e.g. about 55-60° C.) after which the resulting emulsion may be cooled, e.g. to about 40° C., and crystallisation may be induced by seeding and the free base may thereafter be isolated.

In certain embodiments of the invention that may be mentioned, one or more of the following statements may apply to the process of the invention (i.e. the first aspect of the invention).

(a) The process is performed in the presence of formamidine acetate.
(b) $L^1$ represents bromo.
(c) The process is performed in a solvent which is a mixture of IPA liquid ammonia, such as a 6 to 12% by weight of mixture of liquid ammonia in IPA (e.g. about 8.3% by weight or, particularly, about 10.4% by weight of liquid ammonia in IPA).
(d) The process is performed at a temperature of from about 70 to about 90° C. (such as from about 75 to about 85° C., e.g. from about 77 to about 83° C.).
(e) The process includes the step of adding the compound of formula II to a preheated mixture of the solvent(s) and the formamidine (or a salt or derivative thereof), ammonium chloride/formic acid or the like, wherein the preheated mixture may be at a temperature of from about 70 to about 90° C. (such as from about 75 to about 85° C., e.g. from about 77 to about 83° C.).

(f) The process of the invention is performed in a sealed container and, optionally, at elevated pressure.

In a particular embodiment that may be mentioned, statements (c) to (f) above each apply to the process of the invention. In a more particular embodiment, statements (a) to (f) above each apply to the process of the invention.

In the process of the first aspect of the invention, it is preferred that $L^1$ represents halo, especially bromo. Compounds of formula II are novel and hence, in a second aspect of the invention, there is provided a compound of formula II.

Particular compounds of formula II that may be mentioned include a compound of formula IIa:

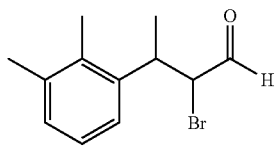

IIa

In a third aspect of the invention, novel compounds of formula II may be prepared from compounds of formula III,

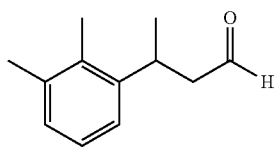

III

Compounds of formula II may be prepared by, for instance, reacting a compound of formula III with an appropriate compound to introduce the $L^1$ group. For instance, in the case of preparation of compounds of formula II in which $L^1$ represents halo, reaction in the presence of an appropriate halogenating reagent (source of halo ions).

To introduce a bromo group (to prepare the most preferred compounds of formula II), an appropriate brominating reagent (i.e. any suitable source of bromide ions) may be employed, for instance 5,5-dibromo barbituric acid.

Alternatively, the brominating agent may be bromine (i.e. $Br_2$). For example, the bromination may be performed in the presence of bromine and a suitable solvent, such as isopropyl acetate and, optionally, in the presence of a suitable complexing agent, such as 1,4-dioxane.

The preparation of novel compounds of formula II may proceed via an intermediate, which intermediate may be a derivative of the compound of formula III. Such intermediates may be formed through the addition of further components to the process, which components may, in particular, be organic compounds and/or catalytic (in respect of the production of compounds of formula II).

In a particular embodiment that may be mentioned, the process for preparing novel compounds of formula II from compounds of formula III may be performed in the presence of a compound of formula IIIa, $HN(R^a)R^b$ IIIa wherein:

$R^a$ and $R^b$ both independently represent a $C_{1-6}$ alkyl group optionally substituted with one or more substituents selected from halo, —CN and $C_{1-6}$ alkoxy (wherein the latter group is optionally substituted with one or more fluoro atoms), or $R^a$ and $R^b$ may be taken together to form, together with the nitrogen atom to which they are both attached, a 5- to 7-membered heterocycloalkyl group, optionally containing one or two additional heteroatom-containing groups selected from O, S and $NR^c$ and optionally substituted with one or more substituents selected from halo, —CN, $C_{1-6}$ alkyl and $C_{1-6}$ alkoxy (wherein the latter two groups are optionally substituted with one or more fluoro atoms); and $R^c$ represents H or a $C_{1-6}$ alkyl group, wherein the latter group is optionally substituted with one or more substituents selected from halo, —CN and $C_{1-6}$ alkoxy (wherein the latter group is optionally substituted with one or more fluoro atoms).

Particular compounds of formula IIIa that may be mentioned include those in which $R^a$ and $R^b$ are taken together to form, together with the nitrogen atom to which they are both attached, a 5- to 7-membered (e.g. 6-membered) heterocycloalkyl group optionally containing one or two (e.g. one) additional heteroatom-containing group(s) selected from O, S and $NR^c$ (e.g. one O atom).

More particular compounds of formula IIIa that may be mentioned include morpholine.

Where the process for preparing novel compounds of formula II from compounds of formula III involves the addition of a compound of formula IIIa, the skilled person will appreciate that the reaction may proceed via a compound of formula IIIb,

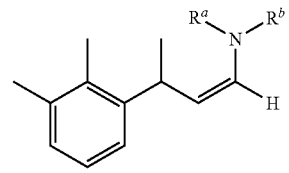

IIIb wherein $R^a$ and $R^b$ are as defined herein in respect of compounds of formula IIIa.

Thus, in a fourth aspect of the invention, novel compounds of formula II may be prepared from compounds of formula IIIb, under conditions as herein described in respect of the preparation of compounds of formula II from compounds of formula III.

Particular compounds of formula IIIb that may be mentioned include compounds of formula IIIc,

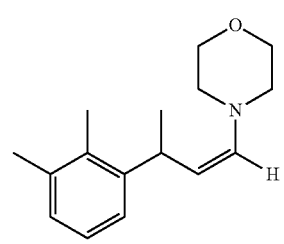

IIIc

In particular, where the process involves the addition of a compound of formula IIIa and/or proceeds via (or starting from) a compound of formula IIIb, the reaction may first involve addition of a compound of formula IIIa to a compound of formula III in the presence of a suitable solvent and, optionally, under conditions suitable for the removal of water from the reaction mixture (for example, wherein the solvent is toluene and, following addition of the compound of formula IIIa, the reaction is heated to the reflux point of the solvent under so-called Dean-Stark conditions (i.e. using a Dean-Stark distillation apparatus)).

More particularly, the process may involve addition of an excess (i.e. greater than one equivalent) of the compound of formula IIIa relative to the compound of formula III, such as about 1.1 to about 2 equivalents (e.g. about 1.5 equivalents).

Alternatively, certain compounds of formula IIIa (such as morpholine) may also be used as the suitable solvent (e.g. where the reaction is performed under conditions suitable for the removal of water from the reaction mixture, such as under Dean-Stark conditions).

The skilled person will understand that compounds of formula IIIb (such as compounds of formula IIIc) can be prepared by an analogous process (e.g. in respect of the preparation of compounds of formula IIIc, addition of morpholine to a solution of a compound of formula III in toluene, followed by heating at the reflux point of the solvent under Dean-Stark conditions).

For the process for the conversion to the compound of formula II in which $L^1$ represents bromo (in particular, where the process does not involve the addition of a compound of formula IIIa and/or proceed via a compound of formula IIIb), the compound of formula III may be reacted in the presence of 5,5-dibromo barbituric acid, for instance such that there is at least one equivalent of bromide ions in the reagent employed (e.g. where the reagent provides two equivalents of the halide ion, then about 0.5 equivalents, compared to the compound of formula III, may be employed). The compound of formula III may first be dissolved in an appropriate solvent (e.g. a polar aprotic solvent such as an ether, especially tetrahydrofuran (THF)) and a small molar equivalent of HCl (e.g. 37% HCl) may be added. This mixture may first be heated (e.g. to above 40° C., such as about 60° C. or up to the boiling point of the solvent), after which the appropriate halogenating (e.g. brominating) reagent (e.g. 5,5-dibromo barbituric acid) may be added. Preferably, it is added in portions such that the temperature (when the reaction is performed in e.g. THF) is kept below the boiling point i.e. below about 65° C. The desired product may be isolated by a work up procedure, e.g. as described in the examples hereinafter.

Alternatively, for the process for the conversion of the compound of formula III to the compound of formula II in which $L^1$ represents bromo (in particular, where the process involves the addition of a compound of formula IIIa and/or proceeds via (or starting from) a compound of formula IIIb), the reaction may be performed in the presence of bromine (i.e. $Br_2$) and, optionally, a suitable solvent (such as ethyl acetate). In particular, such reactions may be performed in the presence of least one equivalent of bromine (i.e. one equivalent of $Br_2$) relative to the compound of formula III, such as a slight excess of bromine (e.g. about 1.01 to about 1.05 equivalents, such as about 1.04 equivalents).

Compounds of formula III and IIIb (e.g. compounds of formula IIIc) may be novel. Thus, in a fifth aspect of the invention, there is provided a compound of formula III, IIIb or IIIc.

In a sixth aspect of the invention, there is provided a process for the preparation of compounds of formula III, which process comprises reaction of a compound of formula IV,

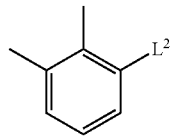

IV in which $L^2$ represents:
(i) halo (most preferably, bromo);
(ii) a group of formula $-N_2X$, wherein X represents a suitable negatively-charged counterion; or
(iii) a structural fragment of the following formula

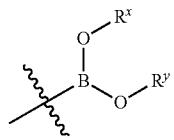

wherein $R^x$ and $R^y$ each independently represent H or a $C_{1-6}$ alkyl, or alternatively $R^x$ and $R^y$ taken together form a $C_{2-3}$ alkylene optionally substituted with one or more methyl, with a compound of formula V (croton aldehyde),

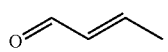

V

As used herein, the skilled person will understand that the bond intersected with the wavy line denotes the bond forming the point of attachment to the remainder of the molecule.

In a first embodiment that may be mentioned, $L^2$ represents halo (most preferably, bromo).

In particular, in the first embodiment the reaction may first proceed via the reaction of a compound of formula IV in which $L^2$ represents halo in order to form a metalated derivative thereof. For example, the compound of formula IV may be reacted with a suitable lithiation agent (such as an organolithium reagent, e.g. n-butyl lithium) to form a derivative of a compound of formula IV in which $L^2$ is replaced by Li.

More particularly, in the first embodiment the reaction may first proceed via the reaction of a compound of formula IV in which $L^2$ represents halo with a Grignard-forming reagent to form the corresponding —Mg-halo derivative (e.g. the corresponding —Mg—Br compound). For example, the reaction may be performed in the presence of THF and the compound of formula IV may be added to Mg (in excess) in THF, which step may also (optionally) comprise the addition of a suitable additive, such as vitride (sodium bis(2-methoxyethoxy)aluminumhydride). In particular, vitride (which may be added as a solution in toluene (e.g. a 65% by weight solution)) may be added in an amount that is less than one equivalent relative to the compound for formula IV (such as from 0.1 to 0.2 equivalents).

For the avoidance of doubt, the skilled person will understand the term Grignard-forming reagent as used herein (which may also be referred to as a Grignard reagent) as referring to any reagent capable of forming the corresponding —Mg-halo derivative of the compound of formula IV, i.e. a derivative of the compound of formula IV having the structural formula:

in which $L^2$ represents halo (e.g. bromo).

In a more particular first embodiment that may be mentioned, the reaction:
(i) first proceeds via the reaction of a compound of formula IV in which $L^2$ represents halo (e.g. bromo) with a Grignard-forming reagent to form the corresponding —Mg-halo derivative (this reaction may be performed in the presence of THF and the compound of formula IV may be added to Mg (in excess) in THF at such a rate that, preferably, the reaction temperature is kept below the boiling point of the solvent, preferably below about 50° C.; after addition is complete the reaction may be heated at elevated temperature for a period of time, e.g. 1 hr, and then cooled to e.g. about −20 to +20° C. (e.g. from about −15 to −20° C., such between about −15 to −20° C. as in the example hereinafter), preferably about −10 to +10° C., most preferably, from about −5 to about +5° C. (e.g. between about −5 to +5° C.));
(ii) followed by reaction with $MnCl_2$ (which is employed in a molar ratio that is about, or near, 1:1, e.g. it is preferably from 3:2 to 2:3, such as between 1.5:1 and 1:1.5) to form the corresponding —MnCl derivative (which may be formed in situ and need not be isolated; and wherein the manganese chloride reagent is preferably added portion-wise so as to preferably keep the temperature in the range about −20 to +20° C. (e.g. from about −15 to −20° C., such as between about −15 to −20° C. as in the example hereinafter), preferably about −10 to +10° C., most preferably, from about −5 to +5° C. (e.g. between about −5 to +5° C.));
(iii) thereafter, TMSCl (in excess) is added (or another suitable reagent, such as an alternative silyl halide), a catalyst (e.g. CuCl; catalytic amount) is added, and then the compound of formula V (which is added as a solution in THF) such that the temperature is again preferably maintained in the range about −20 to +20° C. (e.g. from about −15 to −20° C., such as between about −15 to −20° C. as in the example hereinafter), preferably about −10 to +10° C., most preferably, from about −5 to +5° C. (e.g. between about −5 to +5° C.); and
(iv) upon completion, the desired product may be isolated following an acidic work-up procedure.

In a second embodiment that may be mentioned:
(a) $L^2$ represents halo (most preferably, bromo) or a group of formula —$N_2X$, wherein X represents a suitable negatively-charged counterion (such as or $BF^{4-}$; and
(b) the reaction is conducted in the presence of a suitable catalyst (such as a suitable palladium (e.g. Pd(0) or Pd(II)) catalyst).

In particular, in respect of the second embodiment:
where $L^2$ represents halo (most preferably, bromo), the suitable catalyst may be a Pd(0) catalyst (such as bis(tri-tert-butyl phosphine) palladium),
wherein the catalyst is employed in an amount that is less than one equivalent relative to the compound of formula IV (such as from about 0.001 to 0.01 equivalents, such as about 0.005 equivalents),
optionally in the presence of suitable base, such as triethylamine (which may be employed in an amount that is greater than one equivalent relative to the compound of formula IV, such as from about 1.1 to about 1.5 equivalents (e.g. about 1.3 equivalents), and a suitable solvent (such as THF or, particularly, 2-methyl tetrahydrofuran),
for example at elevated temperature, such as from about 70 to about 90° C. (e.g. at about 80° C.);
where $L^2$ represents a group of formula —$N_2X$ (in particular, wherein X represents $BF^{4-}$), the suitable catalyst may be a Pd(II) catalyst (such as palladium acetate), wherein the catalyst is employed in an amount that is less than one equivalent relative to the compound of formula IV (such as from about 0.01 to 0.1 equivalents, such as about 0.05 equivalents),
optionally in the presence of a suitable solvent (such as methanol),
for example at elevated temperature, such as from about 30 to about 40° C. (e.g. at about 35° C.).

In a third embodiment that may be mentioned, $L^2$ represents a structural fragment of the following formula

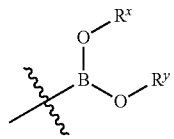

wherein $R^x$ and $R^y$ each independently represent H or a $C_{1-6}$ (e.g. $C_{1-3}$) alkyl, or alternatively
$R^x$ and $R^y$ taken together form a $C_{2-3}$ alkylene optionally substituted with one or more methyl.

In particular, $L^2$ may represent a structural fragment of the above formula wherein $R^x$ and $R^y$ are taken together to form a $C_{2-3}$ (e.g. $C_2$) alkylene optionally substituted with one or more methyl, such as:
(i) a $C_2$ alkylene substituted with four methyl groups;
(ii) an unsubstituted $C_2$ alkylene; and/or
(iii) an unsubstituted (straight chain) $C_3$ alkylene.

Thus, in the third embodiment, there is provided a process for the preparation of compounds of formula III, which process comprises reaction of a compound of formula IVa,

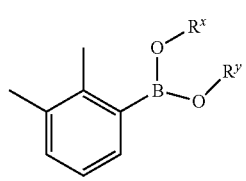

IVa wherein $R^x$ and $R^y$ each independently represent H or a $C_{1-6}$ (e.g. $C_{1-3}$) alkyl, or alternatively
$R^x$ and $R^y$ taken together form a $C_{2-3}$ alkylene optionally substituted with one or more methyl,
with a compound of formula V.

In a fourth embodiment, there is also provided a process for the preparation of compounds of formula III, which process comprises:
(i) preparation of a compound of formula IVa from a compound of formula IV in which $L^2$ represents halo; and then
(ii) reaction of the compound of formula IVa with a compound of formula V.

Thus, there is also provided a process for the preparation of a compound of formula IVa from a compound of formula IV in which $L^2$ represents halo.

In particular, compounds of formula IVa that may mentioned include those wherein $R^x$ and $R^y$ are taken together to form a $C_{2-3}$ (e.g. $C_2$) alkylene optionally substituted with one or more methyl, such as:
(i) a $C_2$ alkylene substituted with four methyl groups;
(ii) an unsubstituted $C_2$ alkylene; and/or
(iii) an unsubstituted (straight chain) $C_3$ alkylene.

Thus, particular compounds of formula IVa that may be mentioned include compounds of formula IVb,

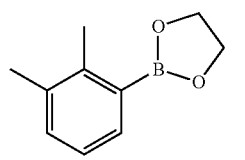

IVb

Compounds of formula IVa may be produced by reaction of the corresponding compound of formula IV in which $L^2$ represents halo (e.g. bromo) or a corresponding metalated derivative thereof (which may be obtained via processes as described in the first embodiment) with a suitable borate, optionally followed by reaction with a suitable alcohol or diol (i.e. an alkyl compound containing two —OH groups).

In particular, compounds of formula IVa may be produced by reaction of the corresponding —Mg-halo derivative (e.g. the corresponding —Mg—Br derivative) of a compound of formula IV (which may be obtained via processes as described in the first embodiment) with trimethylborate, optionally followed by reaction with a suitable diol, such as pinacol (where $R^x$ and $R^y$ form $C_2$ alkylene substituted by four methyl groups) or, more particularly, ethylene glycol (where $R^x$ and $R^y$ form unsubstituted $C_2$ alkylene) or propylene glycol (where $R^x$ and $R^y$ form unsubstituted $C_3$ alkylene).

For example, compounds of formula IVa may be prepared by addition of a reaction mixture obtained following production of the —Mg-halo derivative of a compound of formula IV to a solution of the trimethylborate in a suitable solvent (e.g. the same solvent as used in the production of —Mg-halo derivative (e.g. THF)) or vice versa (for example, wherein the addition is conducted at reduced temperature, such as at about −25° C. and/or maintaining the temperature during the addition at about −10° C. to about −30° C. (e.g. about −20° C.)).

More particularly, the process may involve addition of:
(a) an excess (i.e. greater than one equivalent) of the trimethylborate relative to the compound of formula IV, such as about 1.5 to about 2.5 equivalents (e.g. about 2 equivalents); and/or
(b) optionally, an excess (i.e. greater than one equivalent) of a suitable alcohol or diol (e.g. a suitable diol, such as ethylene glycol), such as at least 10 equivalents (e.g. about 11 equivalents).

Following the addition of the reaction mixture obtained following production of the —Mg-halo derivative to a solution of the trimethylborate (or vice versa), the temperature may be adjusted to about 20-30° C. and any excess solvents/reagents (such as the reaction solvent (e.g. THF), excess trimethylborate and/or methanol produced during the reaction) may be removed from the reaction mixture via distillation, which distillation process may further comprise the addition of a diol, such as ethylene glycol (wherein the distillation temperature is increased to above about 40° C.) and/or toluene (wherein the distillation temperature is increased to above about 110° C.), reflux in the additional solvents for a further period (e.g. of at least 8 hours), filtration of the reaction mixture (e.g. through molecular sieves, such as 4Å molecular sieves) and removal of the diol (e.g. ethylene glycol) fraction of the solvent mixture (which final step may be repeated one or more times through addition and subsequent removal of further portions of ethylene glycol).

In particular, the preparation of compounds of formula III from (or via the synthesis of) a compound of formula IVa may involve reaction of a compound of formula IVa with a compound of formula V in the presence of a suitable catalyst, such as bis(acetonitrile)(1,5-cyclooctadiene)rhodium(I) tetrafluoroborate (e.g. where $R^x$ and $R^y$ are taken together to form a $C_{2-3}$ (e.g. $C_2$) alkylene optionally substituted with one or more methyl) or palladium acetate (e.g. where $R^x$ and $R^y$ both represent H).

More particularly, the preparation of compounds of formula III from (or via the synthesis of) a compound of formula IVa may involve reaction of a compound of formula IVa with a compound of formula V in the presence of a suitable catalyst, such as bis(acetonitrile)(1,5-cyclooctadiene)rhodium(I) tetrafluoroborate, and optionally in the presence of a suitable base, such as sodium bicarbonate, and in the presence of a suitable solvent(s), such as methanol and water.

For example, the preparation of compounds of formula III from (or via the synthesis of) a compound formula IVa may involve addition of the catalyst (e.g. bis(acetonitrile)(1,5-cyclooctadiene)rhodium(I) tetrafluoroborate) to a solution of the compound of formula IVa, the compound of formula V and the suitable base (e.g. sodium bicarbonate) in the suitable solvent(s) (such as a mixture of methanol and water) at about room temperature (e.g. about 25° C.), optionally under an inert atmosphere (such as a nitrogen atmosphere), followed by reaction at elevated temperature (e.g. at above room temperature, for example wherein the temperature is maintained at about 40° C. (using heating or cooling as required), for a period of time, e.g. for about 1 to 4 hours).

Following the reaction of the compound of formula IVa with the compound of formula V, the compound of formula III may be obtained via a work-up procedure comprising addition of butylated hydroxytoluene (BHT) and triethanolamine, removal of additional solvents by heating under reduced pressure, addition of further toluene and triethanolamine solution in water, heating to elevated temperature (e.g. above room temperature, such as about 70° C., for a period of time, e.g. for about 15 minutes), followed by removal of the aqueous portion of the reaction mixture (which latter two steps may be repeated one or more times following the addition of further portions of triethanolamine solution in water) and removal of the remaining solvent (e.g. toluene) via distillation at reduced pressure.

In a particular embodiment that may be mentioned, the preparation of compounds of formula III by reaction of compounds of formula IV via the synthesis of a compound formula IVa proceeds by
(a) reaction of a compound of formula IV with a Grignard reagent to form the corresponding —Mg-halo derivative (this reaction may be performed in the presence of THF and the compound of formula IV may be added to Mg (in excess) in THF at such a rate that, preferably, the reaction temperature is kept below the boiling point of the solvent, preferably below about 50° C.; after addition is complete the reaction may be heated at elevated temperature for a period of time, e.g. 1 hr, and then cooled to e.g. about 20 to 40° C. (e.g. between about 25 to about 30° C. as in the example hereinafter);
(b) reaction of the —Mg-halo derivative of a compound of formula IV trimethylborate in the presence of a suitable solvent (such as THF) and at reduced temperature (for example, at between about −20 to −30° C. (e.g. to about −25° C.)) (in particular, wherein the reaction may employ an excess of the trimethylborate relative to the compound of formula IV, such as about 2 equivalents) to form a compound of formula IVa (this reaction may be performed by addition of the reaction mixture obtained following production of the —Mg-halo derivative to a solution of the trimethylborate in a suitable solvent (e.g. the same solvent as used in the production of —Mg-halo derivative (e.g. THF)) or vice versa (for example, wherein the addition is conducted at reduced temperature, such as at about −25° C. and/or maintaining the temperature during the addition at about −20° C. or below); and wherein, optionally, following the addition of the reaction mixture obtained following production of the —Mg-halo derivative to a solution of the trimethylborate (or vice versa), the temperature may be adjusted to about 20-30° C. and any excess solvents/reagents (such as the reaction solvent (e.g. THF), excess trimethylborate and/or methanol produced during the reaction) may be removed from the reaction mixture via distillation, which distillation process may further comprise the addition of further solvents, such as ethylene glycol (wherein the temperature is increased to above about 40° C.) and/or toluene (wherein the temperature is increased to above about 110° C.), reflux in the additional solvents for a further period (e.g. of at least 8 hours), filtration of the reaction mixture (e.g. through molecular sieves, such as 4Å molecular sieves) and removal of the ethylene glycol fraction of the solvent mixture (which final step may be repeated one or more times through addition and subsequent removal of further portions of ethylene glycol);

(c) reaction of a compound of formula IVa with a compound of formula V in the presence of a suitable catalyst, such as bis(acetonitrile)(1,5-cyclooctadiene)rhodium(I) tetrafluoroborate, and optionally in the presence of a suitable base, such as sodium bicarbonate, and in the presence of a suitable solvent(s), such as methanol and water (this reaction may proceed through the addition of the catalyst (e.g. bis (acetonitrile)(1,5-cyclooctadiene)rhodium(I) tetrafluoroborate) to a solution of the compound of formula IVa, the compound of formula V and the suitable base (e.g. sodium bicarbonate) in the suitable solvent(s) (such as a mixture of methanol and water) at about 25° C., optionally under an inert atmosphere (such as a nitrogen atmosphere), followed by reaction at elevated temperature (e.g. at above room temperature, such as at about 40° C., for a period of time, e.g. for about 1 to 4 hours); for example wherein, following the reaction of the compound of formula IVa with the compound of formula V, the compound of formula III may be obtained via a work-up procedure comprising addition of butylated hydroxytoluene (BHT) and triethanolamine, removal of additional solvents by heating under reduced pressure, addition of further toluene and triethanolamine solution in water, heating to elevated temperature (e.g. above room temperature, such as about 70° C., for a period of time, e.g. for about 15 minutes), followed by removal of the aqueous portion of the reaction mixture (which latter two steps may be repeated one or more times following the addition of further portions of triethanolamine solution in water) and removal of the remaining solvent (e.g. toluene) via distillation at reduced pressure).

In a further embodiment that may be mentioned, the preparation of compounds of formula III by reaction of compounds of IVa proceeds as described in step (c) above.

Certain compounds of formula IVa may be novel. Thus, in a seventh aspect of the invention, there is provided a compound of formula IVa wherein $R^x$ and $R^y$ each independently represent a $C_{1-6}$ (e.g. $C_{1-3}$) alkyl, or alternatively $R^x$ and $R^y$ taken together form a $C_{2-3}$ (e.g. $C_2$) alkylene.

In a particular embodiment, there is provided a compound of formula IVa wherein $R^x$ and $R^y$ are taken together to form a $C_{2-3}$ (e.g. $C_2$) alkylene optionally substituted with one or more methyl, such as:
(i) a $C_2$ alkylene substituted with four methyl groups;
(ii) an unsubstituted $C_2$ alkylene; and/or
(iii) an unsubstituted (straight chain) $C_3$ alkylene.

In a more particular embodiment, there is provided a compound of formula IVb.

In an eighth aspect of the invention, there is provided a process for the preparation of compounds of formula II, which process comprises reaction of a compound of formula IV,

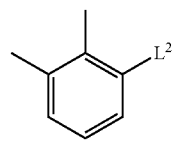

IV in which $L^2$ represents a group of formula —$N_2X$, wherein X represents halo, with a compound of formula V (croton aldehyde),

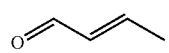

V in the presence of a suitable catalyst.

In a particular embodiment, the suitable catalyst may be a copper salt (such as copper chloride).

In a more particular embodiment, there is provided a process for the preparation of compounds of formula II in which $L^1$ represents chloro, wherein:
(a) X represents Cl; and
(b) the suitable catalyst is a copper salt (such as copper chloride), wherein the catalyst is employed in an amount that is less than one equivalent relative to the compound of formula IV (such as between about 0.01 and 0.1 equivalents, such as about 0.06 equivalents),
optionally wherein the reaction is performed in the presence of suitable acid, such as HCl (which may be employed in an amount that is between about 0.6 and about 1.5 equivalents (e.g. about 0.9 equivalents), and a suitable solvent (such as water), for example at reduced temperature, such as at about 0 to about 10° C. (e.g. at about 0 to about 5° C.).

Where $L^2$ represents a group of formula —$N_2X$, the skilled person will appreciate that the relevant reaction may first comprise the step of forming the —$N_2X$ group from a compound bearing a corresponding amine group. For example, where X represents Cl⁻, the reaction may comprise the step of reacting the corresponding aniline (i.e. 2,3-dimethylaniline) with a suitable diazonium forming reagent, such as sodium nitrite, under conditions known to those skilled in the art, such as in the presence of a suitable acid (such as a mixture of acetic acid and HCl) in a suitable solvent (such as water).

For the avoidance of doubt, it is specifically contemplated that one or more of the processes described herein may be combined in order to provide a single (e.g. multiple step) process. For example, it is specifically contemplated that:

the compound of formula II used in the process of the first aspect of the invention (i.e. the process of the invention) may be prepared using a process as described in the third or fourth aspects of the invention (or any embodiment(s) thereof); and/or the compound of formula III used in the process of the third aspect of the invention (or used in order to prepare the compound of formula IIIa used in the process of the fourth aspect of the invention) may be prepared using a process as described in the sixth aspect of the invention (or any embodiment(s) thereof).

It will be appreciated by those skilled in the art that, in the processes described above, functional groups of intermediate compounds may be, or may need to be, protected by protecting groups.

The protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

The process of the invention may be performed with or without separation (e.g. isolation) of any intermediate products.

The processes described herein may be operated as a batch process or operated as a continuous process and may be conducted on any scale.

Certain embodiments of the invention that may be mentioned include those as defined in the following numbered paragraphs.

Paragraph 1. A process for the preparation of a compound of formula I,

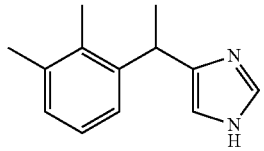

which process comprises reaction of a compound of formula II,

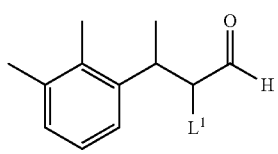

wherein:
L$^1$ represents a suitable leaving group, such as a suitable halo group, a sulfonate group, an oxy-acyl group or the like,
in the presence of:
(a) a source of formamidine, such as formamidine (or a salt or derivative thereof, such as formamidine acetate, formamidine hydrohalide and/or formamidinesulfinic acid) or a mixture of an ammonium salt (e.g. an ammonium halide, such as ammonium chloride) and formic acid; or
(b) formamide.

Paragraph 2. A process as referred to in Paragraph 1, wherein L$^1$ represents bromo.

Paragraph 3. A process as referred to in Paragraph 1 or Paragraph 2, wherein the process is performed in the presence of formamidine acetate.

Paragraph 4. A process as referred to in any one of Paragraphs 1 to 3, wherein the process is performed in a solvent which is a mixture of IPA liquid ammonia, such as a 6 to 12% by weight of mixture of liquid ammonia and IPA (e.g. about 8.3% by weight or, particularly, about 10.4% by weight of liquid ammonia in IPA).

Paragraph 5. A process as referred to in any one of Paragraphs 1 to 4, wherein the process is performed at a temperature of from about 70 to 90° C. (such as 75 to about 85° C., e.g. about 77 to about 83° C.).

Paragraph 6. A process as referred to in any one of Paragraphs 1 to 5, wherein the process includes the step of adding the compound of formula II to a preheated mixture of the solvent(s) and the source of formamidine, wherein the preheated mixture may be at a temperature of from about 70 to 90° C. (such as 75 to about 85° C., e.g. about 77 to about 83° C.).

Paragraph 7. A process as referred to in any one of Paragraphs 1 to 6, wherein the process of the invention is performed in a sealed container and, optionally, at elevated pressure.

Paragraph 8. A compound of formula IIa:

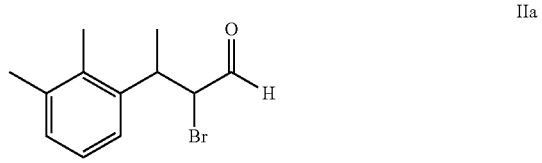

Paragraph 9. A process for the preparation of a compound of formula II in which L$^1$ represents bromo (as referred to in Paragraph 8), which process comprises bromination of a compound of formula III,

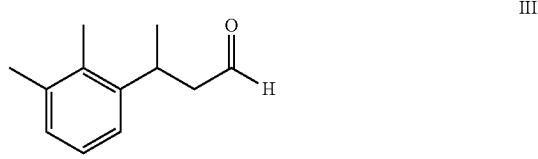

Paragraph 10. A process as referred to in Paragraph 9, wherein the bromination is performed in the presence of 5,5-dibromo barbituric acid.

Paragraph 11. A process as referred to in Paragraph 9, wherein the reaction is performed in the presence of a compound of formula IIIa,

wherein:
R$^a$ and R$^b$ both independently represent a C$_{1-6}$ alkyl group optionally substituted with one or more substituents selected from halo, —CN and C$_{1-6}$ alkoxy (wherein the latter group is optionally substituted with one or more fluoro atoms), or $R^a$ and $R^b$ may be taken together to form, together with the nitrogen atom to which they are both attached, a 5- to 6-membered heterocycloalkyl group, optionally containing one or two additional heteroatom-containing groups selected from O, S and $NR^c$ and optionally substituted with one or more substituents selected from halo, —CN, $C_{1-6}$ alkyl and $C_{1-6}$ alkoxy (wherein the latter two groups are optionally substituted with one or more fluoro atoms); and $R^c$ represents H or a $C_{1-6}$ alkyl group, wherein the latter group is optionally substituted with one or more substituents selected from halo, —CN and $C_{1-6}$ alkoxy (wherein the latter group is optionally substituted with one or more fluoro atoms).

Paragraph 12. A process as referred to in Paragraph 11, wherein:
(a) the compound of formula IIIa is morpholine; and/or
(b) the reaction is performed in the presence of bromine.

Paragraph 13. A process as referred to in Paragraphs 9 or 11, wherein the reaction proceeds via a compound of formula IIIb,

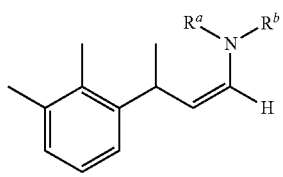

IIIb wherein $R^a$ and $R^b$ are as defined herein in respect of compounds of formula IIIa.

Paragraph 14. A process for the preparation of a compound of formula II in which $L^1$ represents bromo (as referred to in Paragraph 8), which process comprises bromination of a compound of formula IIIb,

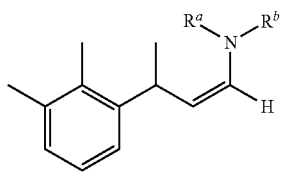

IIIb wherein $R^a$ and $R^b$ are as defined herein in respect of compounds of formula IIIa.

Paragraph 15. A process as referred to in Paragraphs 13 or 14, wherein:
(a) the compound of formula IIIb is a compound of formula IIIc,

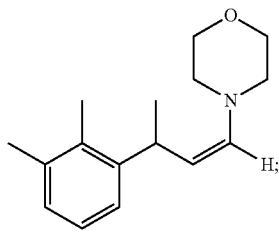

IIIc and/or
(b) the reaction is performed in the presence of bromine.

Paragraph 16. A compound of formula III as defined in Paragraph 9, or a compound of formula IIIb or IIIc, as defined in any one of Paragraphs 13 to 15.

Paragraph 17. A process for the preparation of a compound of formula III as defined in Paragraph 5, which process comprises reaction of a compound of formula IV,

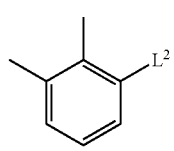

IV in which $L^2$ represents:
(i) halo (most preferably, bromo);
(ii) a group of formula —$N_2X$, wherein X represents a suitable negatively-charged counterion (such as $Br^{4-}$); or
(iii) a structural fragment of the following formula

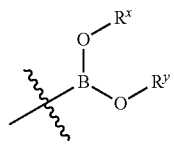

wherein $R^x$ and $R^y$ each independently represent H or a $C_1$ alkyl, or alternatively Rx and $R^y$ taken together form a $C_{2-3}$ alkylene optionally substituted with one or more methyl, with a compound of formula V (croton aldehyde),

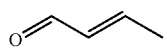

V

Paragraph 18. A process as referred to in Paragraph 17, wherein $L^2$ represents halo (in particular, bromo).

Paragraph 19. A process as referred to in Paragraphs 17 or 18, wherein the process comprises reaction of a compound of formula IVa,

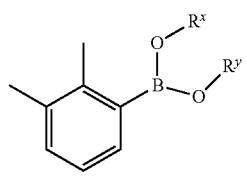

IVa wherein $R^x$ and $R^y$ each independently represent H or a $C_{1-6}$ (e.g. $C_{1-3}$) alkyl, or alternatively
$R^x$ and $R^y$ taken together form a $C_{2-3}$ alkylene optionally substituted with one or more methyl,
with a compound of formula V.

Paragraph 20. A process as referred to in Paragraphs 17 to 19, wherein the reaction comprises:
(a) reaction of a compound of formula IV where $L^2$ represents halo (e.g. bromo) with a Grignard-forming reagent to form the corresponding —Mg-halo derivative;
(b) reaction of the —Mg-halo derivative of a compound of formula IV to form a compound of formula IVa (for example, reaction with trimethylborate in the presence of a suitable solvent (such as THF) and optionally a suitable alcohol or diol and at reduced temperature (for example, at from about −20 to −30° C. (e.g. to about −25° C.)) (in particular, wherein the reaction may employ an excess of the trimethylborate relative to the compound of formula IV, such as about 2 equivalents)); and (c) reaction of a compound of formula IVa with a compound of formula V in the presence of a suitable catalyst (for example, in the presence of bis(acetonitrile)(1,5-cyclooctadiene)rhodium(I) tetrafluoroborate, and optionally in the presence of a suitable base, such as sodium bicarbonate, and in the presence of a suitable solvent(s), such as methanol and water).

Paragraph 21. A process as referred to in Paragraph 17 or 19, wherein the reaction comprises:

(a) reaction of a compound of formula IVa (as defined in Paragraph 19) with a Grignard-forming reagent to form the corresponding —Mg-halo derivative;

(b) reaction of the —Mg-halo derivative of a compound of formula IV to form a compound of formula IVa (for example, reaction with trimethylborate in the presence of a suitable solvent (such as THF) and optionally a suitable alcohol or diol and at reduced temperature (for example, at from about −20 to −30° C. (e.g. to about −25° C.)) (in particular, wherein the reaction may employ an excess of the trimethylborate relative to the compound of formula IV, such as about 2 equivalents)); and (c) reaction of a compound of formula IVa with a compound of formula V in the presence of a suitable catalyst (for example, in the presence of bis(acetonitrile)(1,5-cyclooctadiene)rhodium(I) tetrafluoroborate, and optionally in the presence of a suitable base, such as sodium bicarbonate, and in the presence of a suitable solvent(s), such as methanol and water).

Paragraph 22. A process as referred to in Paragraphs 17, 19 or 20, wherein the compound of formula IVa is a compound of formula IVb,

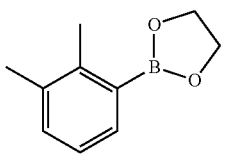

IVb

Paragraph 23. A compound of formula IVa,

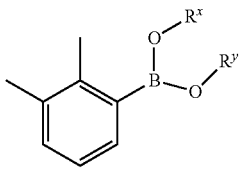

IVa wherein $R^x$ and $R^y$ each independently represent a $C_{1-6}$ (e.g. $C_{1-3}$) alkyl, or alternatively $R^x$ and $R^y$ taken together form a $C_{2-3}$ (e.g. $C_2$) alkylene, or a compound of formula IVb (as defined in Paragraph 22).

Paragraph 24. A process for the preparation of compounds of formula II, which process comprises reaction of a compound of formula IV,

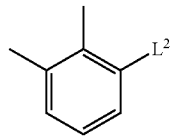

IV in which $L^2$ represents a group of formula —$N_2X$, wherein X represents halo, with a compound of formula V (croton aldehyde),

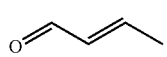

V in the presence of a suitable catalyst (e.g. a copper salt, such as copper chloride).

Paragraph 25. A process as referred to in any one of Paragraphs 1 to 7, wherein the compound of formula II used in the process is prepared using a process as described in any one of Paragraphs 9 to 15.

Paragraph 26. A process as referred to in any one of Paragraphs 9 to 15 or a process as referred to in Paragraph 25, wherein the compound of formula III used in the process is prepared using a process as described in any one of Paragraphs 17 to 22.

Paragraph 27. A process for preparing a formulation comprising a compound of formula I, or a salt thereof, as defined in Paragraph 1, which process is characterised in that it includes a process for preparing a compound of formula I as referred to in any one of Paragraphs 1 to 7 (e.g. Paragraphs 1 to 3), followed by bringing into association the compound of formula I (or a salt thereof) so formed, with the ingredients that form a part of the formulation.

In general, the processes described herein may have one or more of the following advantages.

The compounds of formula I may be produced in a manner that utilises fewer reagents and/or solvents, and/or requires fewer reaction steps (e.g. distinct/separate reaction steps) compared to processes disclosed in the prior art.

Fewer undesired by-products (resultant of undesired side reactions) may be produced, for example, by-products that may be toxic or otherwise dangerous to work with, e.g. explosive.

The processes may also be more economical or efficient that those described in the prior art.

The compound of formula I may be produced in higher yield, in higher purity, in higher selectivity, in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art.

In particular, the use of formamidine and, in particular, formamidine acetate may have the advantage that the process of the invention is improved, e.g. in terms of yield and purity.

There may be several environmental benefits of the process of the invention.

The novel compounds of formula II and III may be produced in high yield and/or with a high degree of regioselectivity, thus providing benefits in respect of, inter alia, the production of the compound of formula I.

The following examples are merely illustrative examples of the processes of the invention described herein.

All equipment, reagents and solvents used were standard laboratory equipment, e.g. glassware, heating apparatus and HPLC apparatus.

EXAMPLES

Example 1

Step 1

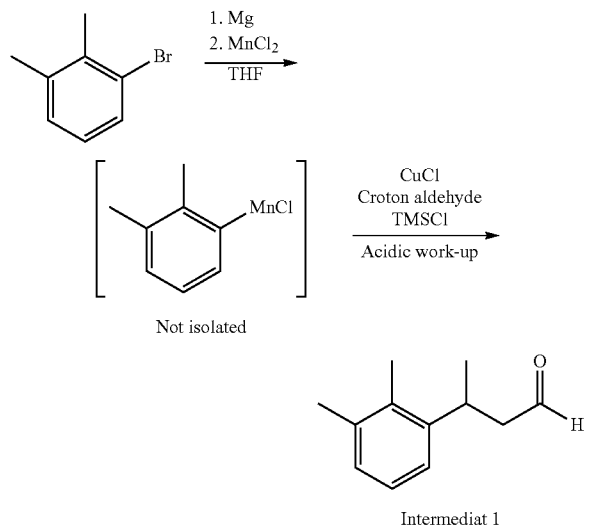

Intermediat 1

Step 2

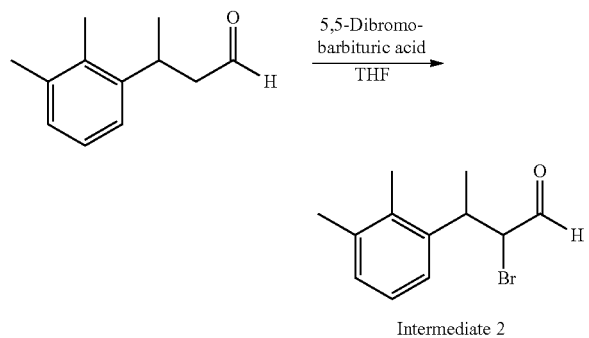

Intermediate 2

Step 3

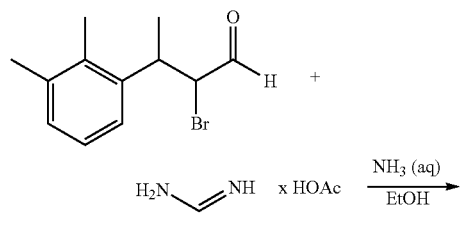

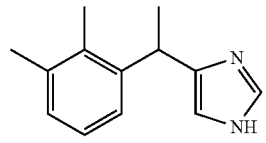

Medetomidine

Step 1

To 131 g, 5.39 mol magnesium in 1.6 L THF is added 100 g, 0.54 mol 2,3-dimethyl bromobenzene as a 10% solution in THF. Once the reaction has started, 900 g, 4.86 mol 2,3-dimethyl bromobenzene as a 10% solution in THF, is added at such rate that the temperature is kept below 50° C. After completion of the addition, the temperature is raised to 60-65° C. for 1 h and then cooled to −15 to −20° C. Manganese chloride, 658 g, 5.23 mol, is added in portions keeping the temperature at −15 to −20° C. To the resulting slurry is added trimethylsilyl chloride, 1118 g, 10.29 mol and CuCl, 16 g, 0.16 mol followed by the slow addition of croton aldehyde, 366 g, 5.22 mol, dissolved in 423 ml THF, over ca 2 h at −15 to −20° C. The mixture is heated to room temperature, diluted with 2 L heptanes and then quenched/hydrolysed by the addition of 2 L water. The water phase is separated and remaining silylenol ether is hydrolysed by stirring the heptane phase with 2 L water containing 155 ml 37% hydrochloric acid for 2 h. After separation of the water phase, 100 mg triethanolamine and 300 mg BHT are added and the solvent stripped at reduced pressure. The residual viscous oil is distilled under reduced pressure to afford 457 g, 2.59 mol, 48%, of intermediate 1.

Step 2

Intermediate 1, 945.8 g, 5.37 mol, is dissolved in 3880 g THF. 37% Hydrochloric acid, 31.2 g, 0.32 mol, is added and the mixture is heated to 60° C. 5,5-Dibromobarbituric acid, 767.6 g, 2.69 mol, is added in portions keeping the temperature below 65° C. The mixture is then stirred for 30 minutes at 60-65° C. THF is stripped under reduced pressure followed by the addition of 2980 g toluene. Residual THF is then distilled under reduced pressure. The toluene phase is washed with 3×3.2 L water followed by 1.6 L 3% aqueous triethanolamine and finally with 1.6 L water. To the toluene phase is added 200 mg triethanolamine and 200 mg BHT. The toluene is stripped at reduced pressure leaving 1150 g, 4.51 mol, 84%, of intermediate 2

Step 3

To a SS pressure reactor is added intermediate 2, 1154 g, 4.53 mol, formamidine acetate, 939 g, 9.02 mol, ethanol, 5280 g and finally 25% aqueous ammonia, 3050 g, 44.9 mol. The mixture is heated at 120° C. for 2 h. Ethanol and ammonia is stripped at atmospheric pressure and the residue dissolved in 1200 ml water and 700 ml ethyl acetate. pH is adjusted to 9-10 with sodium carbonate and the water phase separated. The product is extracted to water by three successive washes with diluted hydrochloric acid. The pH of the acidic aqueous phase is adjusted to 9-10 with sodium carbonate and the product extracted to 500 ml ethyl acetate. The water phase is separated and the ethyl acetate removed at reduced pressure. The residual oil is dissolved in acetone, 4 L, and the product precipitated as the HCl salt by addition of 37% hydrochloric acid to pH 6. Filtration and washing with acetone gives 366 g of Medetomidine×HCl. A second crop of product, 96 g, was isolated by distilling the solvent from the mother liquor followed by the addition of water free acetone. In total, 462 g, 1.95 mol, 43%, of pure Medetomidine×HCl was isolated.

Liberation and Isolation of Medetomidine Free Base

Medetomidine×HCl, 783 g, 3.31 mol, is dissolved in 2.5 L water. Charcoal, 40 g, is added and the mixture stirred for 30 minutes at 70° C. The charcoal is filtered and washed with 0.5 L water. The combined filtrate and washing is diluted with 3.1 L acetone and 0.2 L water. The temperature is adjusted to 55-60° C. and a solution of 132 g, 3.3 mol, sodium hydroxide in 0.54 L water is added over ca 1 h. The resulting emulsion is cooled to ca 40° C. and crystallization is induced by seeding. The slurry is cooled to 0° C., filtered and the filter cake washed with 3×400 ml water. Drying under vacuum afforded 590 g, 2.95 mol, 89%, of Medetomidine free base.

Example 2

The products mentioned herein, e.g. obtained by the procedures disclosed herein (such as those listed in Example 1 above), may be formulated into a suitable end-product, e.g. in the case of the synthesis of the final product medetomidine into an antifouling agent such as Selectope™ using standard formulation. For instance, medetomidine free base may be dissolved in an organic solvent to prepare the final formulated product.

Example 3

Step 1:1

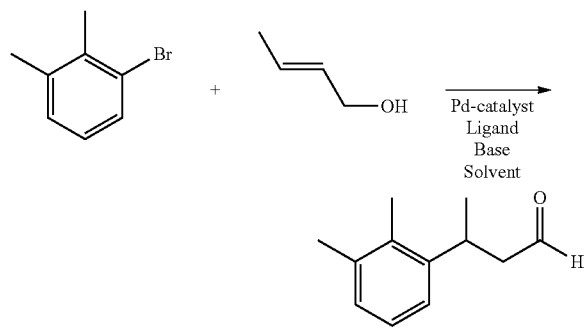

117 g crotyl alcohol (3eq) is dissolved in 400 ml acetonitrile containing 71 g triethylamine (1.3eq). The solution is carefully degassed by a vacuum/nitrogen purge cycle and then heated to 80° C. In another vessel is prepared a solution of 100 g 2,3-dimethylbromo benzene (1eq) in 100 ml 2-MeTHF. The solution is carefully degassed by a vacuum/nitrogen purge cycle and then (bis(tri-tert-butyl phosphine) palladium (0)) (0.005eq) is added. This mixture is added drop-wise over 35 minutes to the crotyl alcohol solution, keeping the temperature at about 80° C. The reaction is cooled to room temperature and quenched by the addition of 308 ml 1% hydrochloric acid followed by extraction of the product to 300 ml MTBE. The MTBE phase is further washed with 2×120 g 16% NaCl solution. The MTBE phase is filtered through Celite followed by evaporation of volatiles at reduced pressure leaving dark yellow oil.

The oil from the experiment above is dissolved in 100 ml ethanol and Girard's reagent T is added in portions until all 3-(2,3-dimethylphenyl)butanal has been converted (HPLC). 0.5eq Girard's reagent T is necessary in order to convert all 3-(2,3-dimethylphenyl)butanal. 300 ml Water, 25 g NaCl and 300 ml MTBE was added. The water phase was separated and washed with 3×150 ml MTBE. The pH of the water phase was adjusted to approximately 1 with 36% HCl, 200 ml MTBE and 36 ml 30% aqueous formaldehyde was added and the mixture stirred at 45° C. until the material was completely converted back to the 3-(2,3-dimethylphenyl)butanal (HPLC). The water phase was separated and the MTBE phase washed 3 times with 100 ml water containing 15 g NaCl. Volatiles were evaporated at reduced pressure leaving 40.8 g of almost colorless oil. Chromatographic purity (HPLC) 95%, yield 43%.

Step 1:2 to 1:5

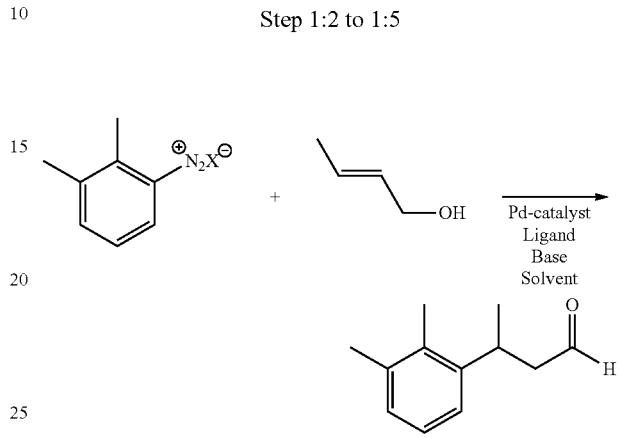

General procedure taken from *Synlett.,* 2009, 6, 973-977.

Step 1:2

Diazonium tertrafluoroborate from 2,3-dimethylaniline is relatively stable and can be used in reaction with crotyl alcohol or its THP derivative e.g. in dimethylformamide and dimethylacetamide. 3-(2,3-Dimethylphenyl)butanal was formed as main product by carrying out the process in the presence of palladium acetate from 0° C. to 40° C. Still, formation of several by-products complicates isolation and purification of the product. Using THP protected crotyl alcohol suppressed formation of some by-products but did not increase the content of target aldehyde in the reaction mixture.

Step 1:3

Crotyl alcohol (0.4 mL; 5 mmol) was dissolved in dimethylformamide (2 mL). Solution was cooled on ice-bath. Diazonium tertrafluoroborate from 2,3-dimethylaniline (2.0 g; 3 mmol) and palladium acetate (0.012 g; 0.05 mmol) were added. Solution was stirred at 1-8° C. for 2 h to obtain dark brown mixture. GC analysis (area %): 3-(2,3-dimethylphenyl)butanal 42%; others 58%.

Step 1:4

Crotyl alcohol (0.4 mL; mol) was dissolved in dimethylacetamide (2 mL). Solution was cooled on ice-bath. Diazonium tetrafluoroborate from 2,3-dimethylaniline (2.0 g; 3 mmol) and palladium acetate (0.012 g; 0.05 mmol) were added. Solution was stirred at 1-8° C. for 4 h to obtain dark brown mixture. GC analysis (area %): 3-(2,3-dimethylphenyl)butanal 24%; others 76%.

Step 1:5

Reaction of THP protected (Z)-2-butene-1,4-diol with diazonium tetrafluoroborate from 2,4-dimethylaniline in the presence of 5 mol % Pd(OAc)2 has been reported to deliver corresponding γ-lactol ether in 68% yield (Synlett, 2009, 6, 973-977). Replication of this procedure gave crude product containing two main compounds with very close retention times and same masses (M=206 by GC-MS as expected; GC area %: 35% and 18%; obviously diastereomers). However, also methoxy-xylene (M=136; GC area %: 6%) and other by-products were formed. Running the experiment above using diazonium salt from 2,3-dimethylaniline, however, gave mixture that contained methoxy-xylene (M=136) as main product (GC area %: 47%) and small amount of isomeric compounds presumed to form by Heck-Matsuda reaction followed by cyclization (M=206; GC area %: 15% and 8%).

Step 1:6

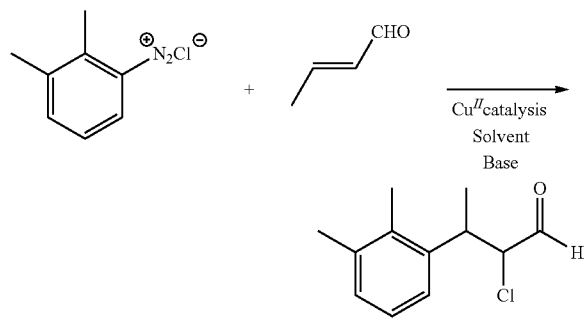

General procedure taken from German patent DE2016809.

12.1 g 2,3-dimethylaniline (1.0 eq) is dissolved in 28 ml acetic acid. A solution is formed. Then, a mixture of 7.0 g of water and 24.7 g of 37% HCl (3.2 eq) is added. A crystal-slurry is formed with evolution of heat. After cooling to <5° a solution of 7.5 g of NaNO2 (1.1 eq) in 15 ml of water is added in portions (under the surface of the crystal-slurry), keeping temperature at 0°-5°. A pale red diazonium salt solution is formed. Then, a mixture of 0.5 g CaO (0.09 eq), 5.1 g croton aldehyde (0.7 eq) and 12 ml acetone is added alternating with a solution of 0.6 g CuCl (0.06 eq) in 7.1 g 37% HCl (0.9 eq) at 0°-5°. A green-yellow solution is formed accompanied by a slow evolution of nitrogen. After ca 5 hours at 0°-5°, cooling are finished and the reaction mixture is allowed to reach room temperature.

Result: Analysis by GC-MS showed no significant formation of wanted 2-chloro-3-(2,3-dimethylphenyl)butanal. Instead, the main products were 3-chloro-1,2-dimethylbenzene, 2,3-dimethylphenol and 2,3-dimethylphenylacetate.

Step 2

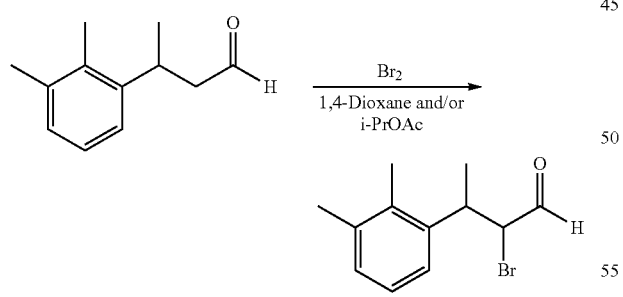

Step 2:1

3-(2,3-Dimethylphenyl)butanal (5.1 g; GC area %. 95%) was dissolved in isopropyl acetate (10 mL). Solution was cooled on ice-bath to 1° C. Solution of bromine (1.75 mL) in isopropyl acetate (10 mL)/dioxane (5 mL) mixture was added portion-wise in 130 min holding temperature of the mixture below 5° C. More isopropyl-acetate (15 mL) was added. Stirring was continued for 1 h. Water (10 mL) was added. Phases were separated. Organic phase was washed with saturated sodium bicarbonate solution (2×10 mL). Colourless cloudy organic solution was obtained; (33.6 g); GC (area %): 0.7% 3-(2,3-dimethylphenyl)butanal; 94.5% 2-bromo-3-(2,3-dimethylphenyl)butanal; 4.8% others. NMR assay: 18.40% of 2-bromo-3-(2,3-dimethylphenyl)butanal; calculated yield: 90%.

Step 2:2

3-(2,3-Dimethylphenyl)butanal (11.5 g; GC area %. 88.7%) was dissolved in isopropyl acetate (40 mL). Solution was cooled on ice-bath to 1° C. 48%. Hydrobromic acid (0.2 mL) was added. Solution of bromine (3.2 mL) in isopropyl acetate (30 mL) was added portion-wise (1 mL) in 100 min holding temperature of the mixture below 5° C. Stirring was continued for 1.5 h. Additional portion of bromine (0.3 mL) in isopropyl acetate (5 mL) was added in 30 minutes. Stirring continued for 30 min. Water (10 mL) was added. Phases were separated. Organic phase was washed with saturated sodium bicarbonate solution (2×20 mL). Almost colourless cloudy organic solution was obtained; (78.2 g); GC (area %): 0.6% 3-(2,3-dimethylphenyl)butanal; 90.5% 2-bromo-3-(2,3-dimethylphenyl)butanal; 8.9% others. NMR assay: 17.2% 2-bromo-3-(2,3-dimethylphenyl)butanal; calculated yield: 91.7%.

Example 4

Step 1

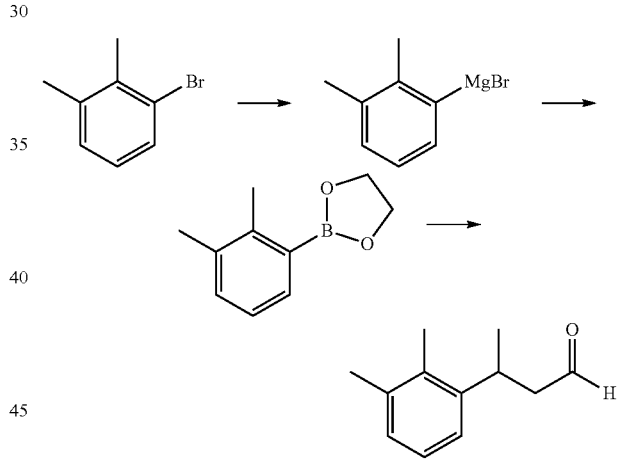

Step 2

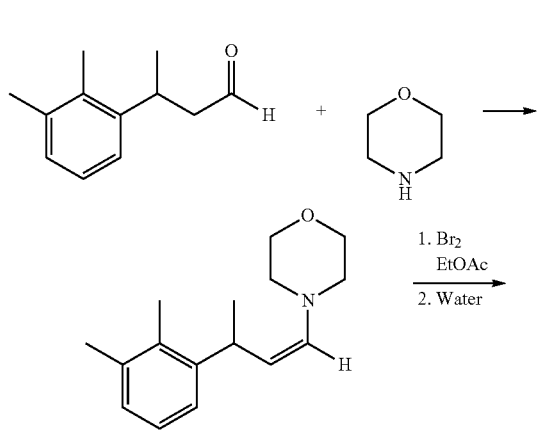

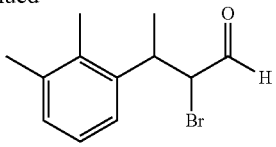

Step 3

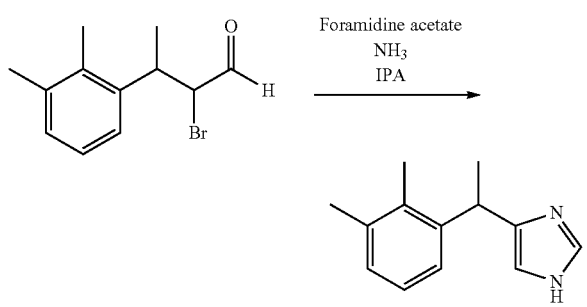

Step 1:1

1-Bromo-2,3-dimethylbenzene (74 g, 0.40 mol) is charged to a reaction vessel and dissolve in THF (204 mL). Inert by applying vacuum (100 mbar) and change atmosphere to nitrogen. Magnesium turnings (9.73 g, 0.40 mol) and THF (201 mL) is charged to a second reaction vessel. Stir at as such a high rate that the Magnesium turnings are swirling in the reactor. To this mixture approximately 10% of the 1-Bromo-2,3-dimethylbenzene/THF solution is charged. Vitride (15 mg) is charged in order to start the reaction. The remaining 1-Bromo-2,3-dimethylbenzene/THF solution is charged during approximately 1 hour at 50° C. The reaction is then stirred for at least one hour. Cool the solution to 25-30° C. The above-prepared Grignard reagent solution is added to a cool (−25° C.) mixture of trimethylborate (90 mL, 0.80 mol) in THF (223 mL). The Grignard reagent solution is then added at such rate that the temperature not exceeds −20° C. Borate ester will start to precipitate during the dosing. Adjust stirring rate so that a good mixing is obtained. Adjust temperature to 20-30° C. and distil off THF, excess trimethylborate, and methanol that are formed during the reaction under vacuum. Charge ethylene glycol (247 mL, 4.4 mol) to the mixture and stir at a temperature above 40° C. until practically all solid matter is dissolved. Continue the distillation at reduced pressure in order to remove the remaining volatile components. Toluene (222 mL) is added and distillation is continuing at atmospheric temperature until temperature in the reactor reaches above 110° C. Reflux at this temperature for at least 15 min. Compensate by charging approximately the same volume toluene that is distilled off. The reaction is then refluxed for at least 8 hours. The condensate is filtered through a filter filled with 4 Å molecular sieves (18 g) before re-entering the reaction.

Adjust temperature to 95-100° C. and allow separating for 15 minutes. Cut the lower ethylene glycol phase Allow the upper phase to stand for 15-30 minutes and cut a further fraction of lower glycol phase if possible. Ethylene glycol (82 g, 1.3 mol) is added and the mixture is stir at 95-100° C. for 15 min. Adjust stirring rate so that a good mixing of the phases is obtained. The phases are then allowed to separate for 15 minutes. Discard the lower ethylene glycol phase. Allow the upper phase to stand for 15-30 minutes and cut a further fraction of lower glycol phase if possible. Ethylene glycol (82 g, 1.3 mol) is once more added and the mixture is stirred at 95-100° C. for 15 min. The phases are then allowed to separate for 15 minutes. Discard the lower ethylene glycol phase. Allow the upper phase to stand for 15-30 minutes and cut a further fraction of lower glycol phase if possible. Cool the solution to below 60° C. and charge methanol (148 mL) and distill off toluene and methanol by azeotropic distillation at 65° C. All charged methanol needs to be distilled off. Cool the reaction to 25° C. and charge fresh methanol (341 mL).

Charge THF (78 mL), sodium bicarbonate (0.24 g) dissolved in water (52 mL), and croton aldehyde (40 g, 0.57 mol) to the reaction mixture at 25° C. Inert by applying vacuum and change atmosphere to nitrogen. This vacuum (100 mbar)/nitrogen cycle are done at least four times.

Charge bis(acetonitrile)(1,5-cyclooctadiene)rhodium(I) tetrafluoroborate (0.11 g) to the mixture at 25° C. Adjust temperature to 40° C. and stir for 1-4 hours. Add BHT (74 mg) and triethanolamine (74 mg) and the solvents are distilled off under reduced pressure until condensation decreases. Charge toluene (185 mL) and a solution of triethanolamine (3 mL) in water (74 mL). Adjust temperature to 70° C. and stir for at least 15 min before the phases are allowed to separate during 15 minutes. Discard the lower water phase. Charge a new portion of triethanolamine (3 mL) in water (74 mL). Adjust temperature to 70° C. and stir for 15 minutes before the phases are allowed to separate at 70° C. during 15 min, discard the lower water phase.

Distill of toluene at reduced pressure until reaching a residual volume of 250 mL. The product (3-(2,3-dimethylphenyl)butanal) solution is filtered. Charge triethanolamine (7 mg)).

The product solution can be used without further purification for preparation of the corresponding 3-(2,3-dimethylphenyl)-2-bromobutanal.

Step 1:2

To 677 g 2-(2,3-dimethylphenyl)-1,3,2-dioxaborolan, 7512 g methanol, 935 g tetrahydrofuran, 3.3 g sodium bicarbonate, 700 g water, and 533 g croton aldehyde are charged. The solution is degassed in three cycles, and the temperature is adjusted to 20° C. Protective inert nitrogen atmosphere is applied and 1.5 g Rh-141 ([Rh(COD)(MeCN)$_2$]BF$_4$) catalyst is charged. The reaction is exothermic and the temperature increases ~20-25° C. The temperature is adjusted to 40° C. and the reaction mixture is stirred for 4-8 hours in order to reach complete conversion. 1 g BHT and 1 g triethanolamine are added and solvents evaporated off under vacuum at 60° C. 2500 ml toluene is charged and the temperature adjusted to 50° C. The toluene layer is washed with 1000 ml water and 50 g triethanolamine, and the water layer separated, cut, and discarded at 70° C. The toluene layer is washed with 1000 ml water and 50 g triethanolamine, and the water layer separated, cut, and discarded at 70° C. Solvents are evaporated off under vacuum at 80° C., giving 657 g of yellow oil. Chromatographic purity (GC) 96.4%, yield 69%.

Step 2

To 3-(2,3-dimethylphenyl)butanal in toluene (82.2 g, 0.28 mol) is added toluene (93 mL) and morpholine (36 mL, 0.42 mol). The mixture is heated to reflux with a Dean-Stark trap mounted in order to remove formed water. When the theoretical amount of water have been removed and no more water is distilled off solvents is distilled off until reaching a residual volume of 110 mL.

To a second reaction vessel is added bromine (15 mL, 0.29 mol) and ethyl acetate (566 mL) and the mixture is cooled below −10° C. To this bromine solution is added the enamine solution prepared above in a rate keeping the temperature below −10° C. After at least 10 minutes of stirring water (185 mL) is added to quench the reaction and then the temperature is increased to 25° C. If necessary the pH is adjusted to below 4 by adding hydrochloric acid. The stirring as the phases are allowed to separate during 10 minutes. The lower phase is discarded. A solution of sodium bicarbonate (7.6 g) and sodium thiosulfate 7.5 g) in water (132 mL) is added and the mixture is stirred for 10 minutes and then the phases are allowed to separate during 10 minutes. The lower phase is discarded. Water (153 mL) is added and the mixture is stirred for 10 minutes before stirring as stopped and the phases are allowed to separate. The lower phase is discarded. BHT (0.1 g) and triethanolamine (0.1 g) is charged. Solvents are distilled of with applied vacuum until a residual volume of 93 mL. The crude product solution containing 62.8 g 2-bromo-3-(2,3-dimethylphenyl)butanal is collected. Overall yield from 1-Bromo-2,3-dimethylbenzene is 61%.

Step 3:1

The reaction was performed in a PTFE-lined bomb. Bromoaldehyde (3.4 g; containing 2.5 g, 9.8 mmoles of bromoaldehyde by NMR assay) and 2.04 g (19.6 mmoles) formamidine acetate were mixed with 30 mL isopropanol containing ammonia (8.3%; 118 mmoles). The mixture was heated on oil-bath at 77-80° C. for 2 h. After cooling to 21° C. GC analysis showed 74.8 area % of Medetomidine and about 11-12% high boiling by-products (including pyrazines).

The reaction mixture was concentrated on rotavapor. To the residue (10.7 g) 15 mL of toluene, 15 mL of water and 1 mL of 30% sodium hydroxide were added. The mixture was warmed to 30° C. and the phases were separated. Lower water phase (pH-11-12) was discarded. Toluene phase was assayed by NMR to give 70% yield of Medetomidine.

Step 3:2

Formamidine acetate (0.25 g) was mixed with 3 mL 10.4% w/w ammonia solution in 2-propanol. The mixture was immersed into oil bath (77° C.). Formamidine acetate dissolved at about 70° C. resulting in colorless solution. Bromoaldehyde (BB-A-12-2K; 0.42 g, calculated to contain 0.31 g of bromoaldehyde) was added with micro syringe during 20 min at 77-80° C. Stirring was continued at 76-81° C. bath temperature for 2 h.

GC analysis of crude product showed 84.5% Medetomidine and 3.7% of high-boiling by-products.

Step 3:3

Formamidine acetate (28.5 g; 0.27 mol) was mixed with 10.4% solution of ammonia in 2-propanol (260 mL; 1.24 mol NH$_3$). Mixture was heated to 83° C. (oil-bath 97° C.). Bromoaldehyde (BB-A-17-3K, 51 g, 0.137 mol) was pumped into the reactor in 42 minutes. Post reaction at 90-91° C. for 2 h.

Reactor was cooled to RT. The mixture contained 80% Medetomidine and 3.2% by-products by GC area % analysis.

Reaction mixture (305.5 g) was concentrated to 112.8 g. To the concentrate 150 mL toluene, 100 mL water and 18 mL 30% NaOH were added. The mixture stirred at 50-55° C. for 10 min and phases were separated. Toluene phase was assayed by NMR to give 81% yield of Medetomidine.

Step 3:4

Formamidine acetate (21 g; 0.20 mol) was mixed with 10.4% solution of ammonia in 2-propanol (250 mL; 1.2 mol of NH$_3$). Mixture was heated in oil-bath to 80° C. (oil-bath 97° C.). Bromoaldehyde (BB-A-17-3K, 50 g; 0.134 mol) was pumped into the reactor in 40 minutes at 85-89° C. After 2 h post reaction the mixture was cooled to RT. The mixture contained 80% Medetomidine and 3.2% by-products by GC area % analysis.

Isolation was carried out as same as described in Step 3:3 (directly above).

Toluene phase was assayed by NMR to give 82.8% yield of Medetomidine.

Abbreviations
BHT butylated hydroxytoluene
eq equivalent(s)
h hour(s)
HPLC high-performance liquid chromatography
IPA isopropyl alcohol
MTBE methyl-tert-butyl ether
NMR nuclear magnetic resonance
PTFE polytetrafluoroethylene
THF tetrahydrofuran

The invention claimed is:

1. A process for the preparation of a compound of formula I,

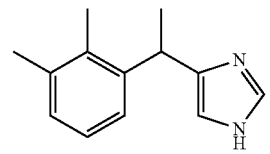

which process comprises reaction of a compound of formula II,

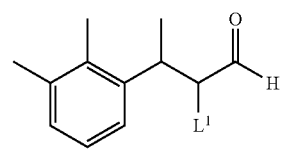

wherein:
 L$^1$ represents a leaving group,
 in the presence of:
 (a) a source of formamidine; or
 (b) formamide.

2. A process as claimed in claim 1, wherein:
 (a) the process is performed in the presence of formamidine, formamidine acetate, formamidine hydrohalide, formamidinesulfinic acid, or a mixture of ammonium chloride and formic acid; and/or
 (b) L$^2$ represents a halo group, a sulfonate group, or an oxy-acyl group.

3. A process as claimed in claim 1 or claim 2, wherein:
 (i) the process is performed in the presence of formamidine acetate; and/or
 (ii) L$^1$ represents bromo.

4. A compound of formula IIa:

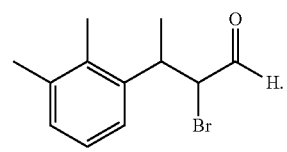

5. A process for the preparation of a compound of formula IIa,

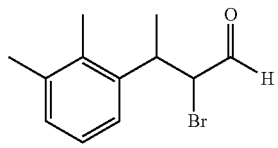

IIa which process comprises bromination of a computer of formula III,

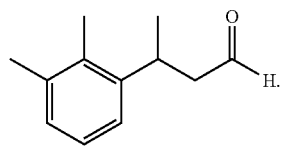

III

6. A process as claimed in claim 5, wherein the bromination is performed in the presence of 5,5-dibromo barbituric acid.

7. A process as claimed in claim 5, wherein the reaction is performed in the presence of a compound of formula IIIa, HN(R$^a$)R$^b$  IIIa wherein:
R$^a$ and R$^b$ both independently represent a C$_{1-6}$ alkyl group optionally substituted with one or more substituents selected from halo, —CN and C$_{1-6}$ alkoxy (wherein the latter group is optionally substituted with one or more fluoro atoms), or R$^a$ and R$^b$ may be taken together to form, together with the nitrogen atom to which they are both attached, a 5- to 6-membered heterocycloalkyl group, optionally containing one or two additional heteroatom-containing groups selected from O, S and NR$^c$
and optionally substituted with one or more substituents selected from halo, —CN, C$_{1-6}$, alkyl and C$_{1-6}$ alkoxy (wherein the latter two groups are optionally substituted with one or more fluoro atoms); and R$^c$ represents H or a C$_{1-6}$ alkyl group, wherein the latter group is optionally substituted with one or more substituents selected from halo, —CN and C$_{1-6}$ alkoxy (wherein the latter group is optionally substituted with one or more fluoro atoms).

8. A process as claimed in claim 7, wherein:
(a) the compound of formula IIIa is morpholine; and/or
(b) the reaction is performed in the presence of bromine.

9. A compound of formula III,

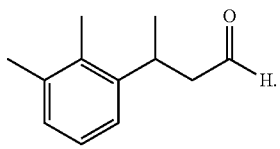

III

10. A process for the preparation of a compound of formula III,

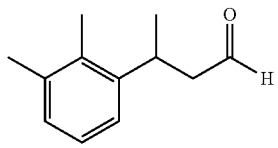

III which process comprises reaction of a compound of formula IV,

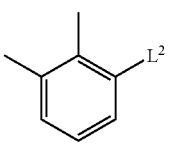

IV in which L$^2$ represents:
(i) halo;
(ii) a group of formula —N$_2$X, wherein X represents a suitable negatively-charged counterion; or
(iii) a structural fragment of the following formula

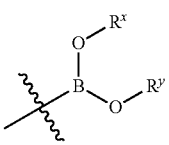

wherein R$^x$ and R$^y$ each independently represent H or a C$_{1-6}$ alkyl, or alternatively R$^x$ and R$^y$ taken together form a C$_{2-3}$ alkylene optionally substituted with one or more methyl,
with a compound of formula V (croton aldehyde),

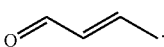

V

11. A process as claimed in claim 10, wherein the process comprises reaction of a compound of formula IVb,

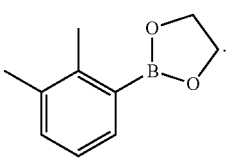

IVb

12. A compound of formula IVa,

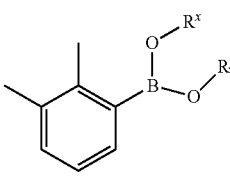

IVa wherein R$^x$ and R$^y$ each independently represent a C$_{1-6}$ alkyl, or alternatively $R^x$ and $R^y$ taken together form a $C_{2-3}$ alkylene, or formula IVb,

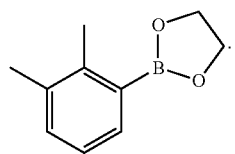

IVb

13. A process for preparing a formulation comprising a compound of formula I, or a salt thereof, as defined in claim 1, which process is characterised in that it includes a process for preparing a compound of formula I as claimed in any one of claims 1 to 3, followed by bringing into association the compound of formula I (or a salt thereof) so formed, with the ingredients that form a part of the formulation.

14. The process of claim 10, wherein (i) halo is bromo.

15. The process of claim 10, wherein X is $BF_4$.

* * * * *

UNITED STATES PATENT AND TRADEMARK OFFICE
CERTIFICATE OF CORRECTION

PATENT NO. : 8,962,862 B2  
APPLICATION NO. : 14/234263  
DATED : February 24, 2015  
INVENTOR(S) : Lars Eklund et al.

Page 1 of 1

It is certified that error appears in the above-identified patent and that said Letters Patent is hereby corrected as shown below:

In the Claims
Column 33, claim 7, line 42, please delete "$C_{1-6}$, alkyl" and replace with --$C_{1-6}$ alkyl--.

Signed and Sealed this
Twenty-first Day of June, 2016

Michelle K. Lee
*Director of the United States Patent and Trademark Office*